(12) United States Patent
Hartig et al.

(10) Patent No.: US 7,479,124 B2
(45) Date of Patent: Jan. 20, 2009

(54) DEVICE FOR TREATMENT OF VENOUS CONGESTION

(75) Inventors: Gregory K. Hartig, Cross Plains, WI (US); Nadine P. Connor, Madison, WI (US); Michael L. Conforti, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 202 days.

(21) Appl. No.: 10/273,215

(22) Filed: Oct. 16, 2002

(65) Prior Publication Data

US 2003/0032919 A1 Feb. 13, 2003

Related U.S. Application Data

(63) Continuation-in-part of application No. 09/745,298, filed on Dec. 20, 2000, now abandoned.

(60) Provisional application No. 60/171,351, filed on Dec. 22, 1999.

(51) Int. Cl.
*A61M 1/00* (2006.01)
*A61M 3/00* (2006.01)
*A61M 37/00* (2006.01)

(52) U.S. Cl. .............................. 604/27; 604/35; 604/43; 604/47

(58) Field of Classification Search .................. 604/19, 604/23, 27, 30, 35, 131, 140, 147, 506, 540–543, 604/239, 264, 266, 268, 272, 269, 28, 43–48, 604/93.01, 514, 275, 285, 286, 902; 600/573, 600/583, 156; 606/115; 128/898

See application file for complete search history.

(56) References Cited

U.S. PATENT DOCUMENTS

| 5,156,597 | A | * | 10/1992 | Verreet et al. ................ 604/175 |
| 5,531,672 | A | * | 7/1996 | Lynn .......................... 604/6.12 |
| 6,156,004 | A | * | 12/2000 | Tremaine et al. .............. 604/27 |
| 6,227,203 | B1 | * | 5/2001 | Rise et al. .................... 128/898 |
| 6,340,354 | B1 | * | 1/2002 | Rambin ........................ 604/22 |
| 6,689,103 | B1 | * | 2/2004 | Palasis ........................ 604/173 |
| 6,878,142 | B2 | * | 4/2005 | Lawrence et al. ............ 604/540 |

FOREIGN PATENT DOCUMENTS

WO   WO 00/78212   12/2000

OTHER PUBLICATIONS

E. Clyde Smoot, et al., Mechanical Leech Therapy to Relieve Venous Congestion, Journal of Reconstructive Microsurgery, vol. 11, No. 1, Jan. 1995.

Carl R. Hartrampf, Jr., M.D., et al., A Mechanical Leech for Transverse Rectus Abdominis Musculocutaneous Flaps, published Apr. 2, 1993.

(Continued)

*Primary Examiner*—Kevin C. Sirmons
*Assistant Examiner*—Catherine N Witczak
(74) *Attorney, Agent, or Firm*—Quarles & Brady LLP

(57) ABSTRACT

A device for treatment of venous congestion provides for subcutaneous introduction of anticoagulant through an incision positioned within a collection shell for withdrawal of an effused material. A widened delivery tip provides dispersal of the anticoagulant and may be agitated to disrupt clot formation.

12 Claims, 4 Drawing Sheets

OTHER PUBLICATIONS

Cottler, Patrick S. et al., Development of a Clinically Useful Mechanical Leech Device that Promotes Flap Survival in an Animal Model of Venous-Congested Skin Flaps, Annals of Plastic Surgery 2001;47:138-147.

Stover, Dawn, Mechanical Leech, article in Popular Science, 2002, printed from Web, www.popsci.com/popsci/medicine/article/0,12543,230229.00.

Cottler, Partick S., Improving on Nature printed from Web www.virginia.edu/insideuva/2000/14/cottler.html.

* cited by examiner

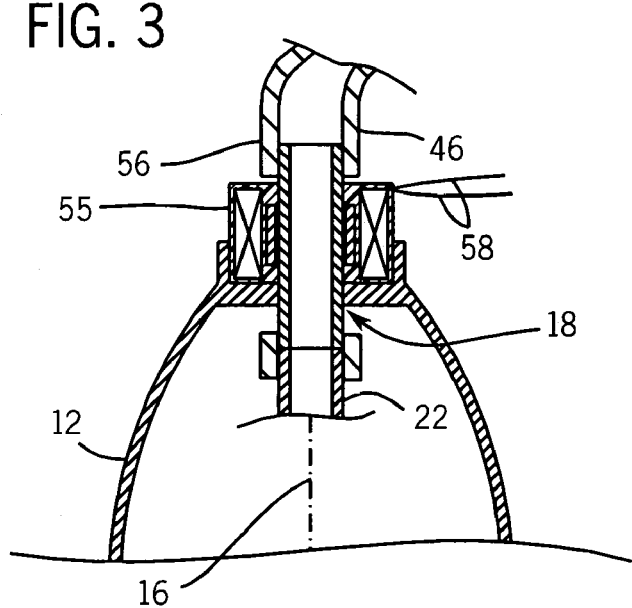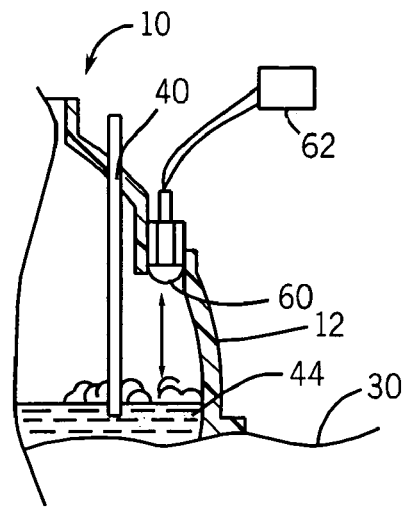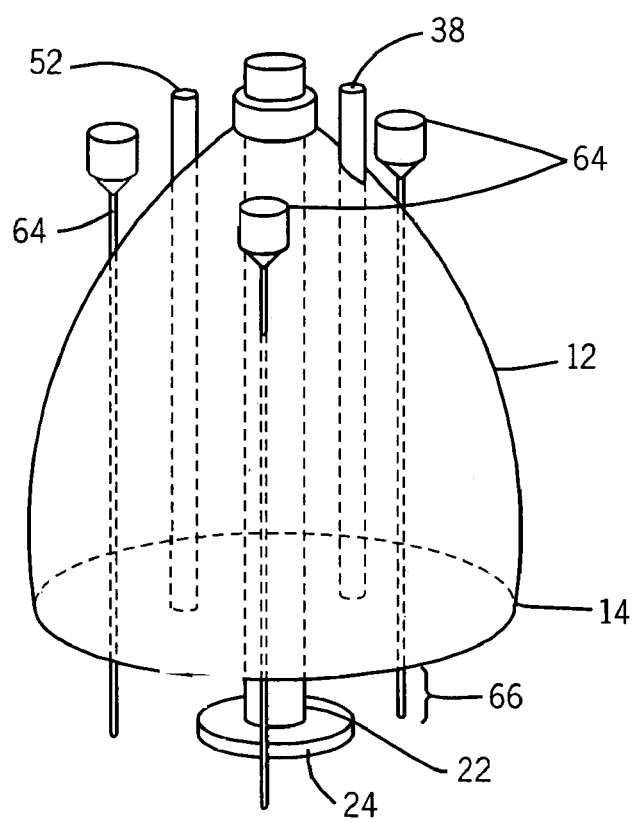

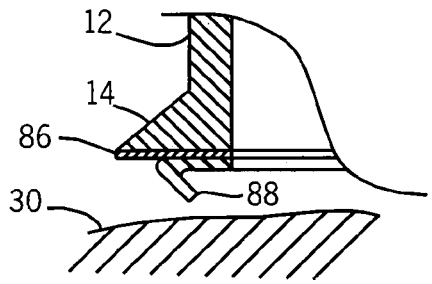
FIG. 8
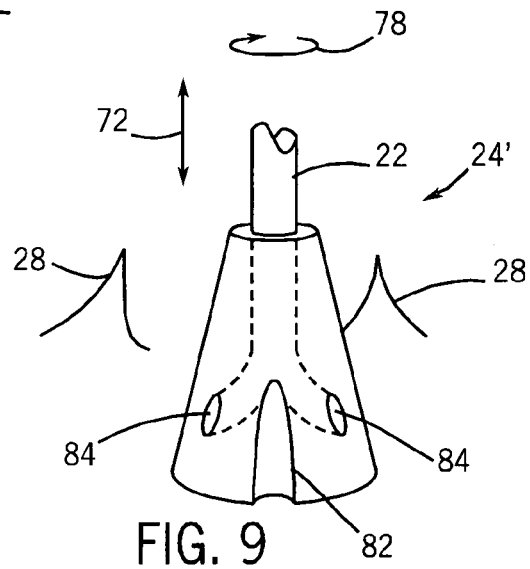
FIG. 9
FIG. 10
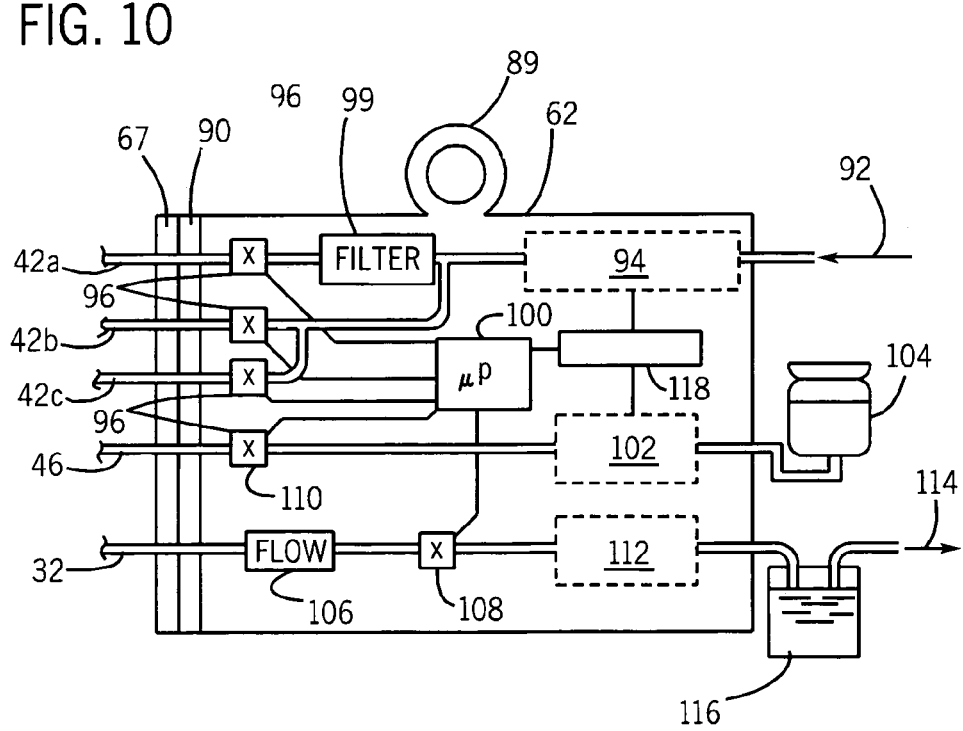

DEVICE FOR TREATMENT OF VENOUS CONGESTION

CROSS-REFERENCE TO RELATED APPLICATIONS

This application is a continuation in part of U.S. application Ser. No. 09/745,298 filed Dec. 20, 2000 which is based on and claims the benefit of U.S. provisional application 60/171,351 filed Dec. 22, 1999.

STATEMENT REGARDING FEDERALLY SPONSORED RESEARCH OR DEVELOPMENT

BACKGROUND OF THE INVENTION

The invention relates generally to medical devices to remove excess blood from congested tissue and particularly to a simple mechanical device to replace medicinal leeches.

A potential post-surgical complication of reconstructive or microvascular surgery is venous congestion. Replanted tissue may become congested due to blood clot formation in the venous outflow of the tissue, or in any situation where arterial inflow exceeds venous outflow. Furthermore, venous stasis or pooling caused by an arterial supply, which is insufficient for the reconstructed tissue can also occur following microvascular surgery. Venous congestion, if not corrected by surgery or some other means, can result in tissue death.

If surgical correction fails, the current method of treating either venous congestion or venous stasis is with live medicinal leeches. The use of leeches can present a number of problems. For example, leeches can move off congested tissue and feed on normal skin, they are difficult to use in or near orifices of the body because of their potential for migration, the quantity of blood removable by a leech is very limited, and leeches may harbor serious pathogens.

Cursory attempts have been made to develop mechanical or chemical replacements for the live medicinal leech. A simple mechanical device was used by Smoot et al. in 1995 (Smoot EC, Ruiz-Inchaustegui JA, Roth AC (1995) Mechanical Leech Therapy to Relieve Venous Congestion. J Reconstr Microsurg 11: 51-55). This device consisted of a small glass bell that was placed over a punch biopsy wound. A fluid passing through an inlet port irrigated the wound and was suctioned off via a suction port at −80 mmHg. Chemical replacements for leech therapy have also been studied. The "chemical leech" involved subcutaneous injections of calcium heparin into the reattached fingers of three patients, with drainage into dressings over the surgical site. (Barnett G. R., Taylor G.I. and Mutimer K.L. (1989). The "chemical leech:" Intra-replant subcutaneous heparin as an alternative to venous anastomosis. Report of three cases. Br J Plast Surg 42:556-558. These subcutaneous injections of anticoagulant were used to promote drainage of excess blood into the dressings of the surgical site. However, prior work has not provided an adequate clinical solution for the post-surgical complication of venous congestion. The need for the development of new techniques is clearly indicated.

SUMMARY OF THE INVENTION

The present invention provides an improved device for the treatment of venous congestion. In one non-limiting embodiment, the device consists of a shell, which acts as a collection chamber and which supports a conduit terminating in a widened delivery tip which supplies anticoagulant subcutaneously through a skin incision.

Specifically, the invention provides a shell having a rim adapted to abut the patient's skin to define a suction area circumscribed by the rim and enclosed by an inner volume of the shell. A conduit is supported by the shell having a delivery tip for the delivery of anticoagulant and saline irrigation positionable subcutaneously below the rim within the suction area when the shell is positioned against the patient's skin, the delivery tip having a larger cross-sectional area than the conduit to disperse the anticoagulant beneath the skin and provide subcutaneous agitation as a means of discouraging or breaking up clot formation. A suction port is attached to the shell through which recovered anticoagulant and blood may be drawn from the inner volume.

Depending on the embodiment, the delivery tip may 1) supply anticoagulant subcutaneously in a controlled fashion, 2) disperse the anticoagulant, 3) provide mechanical anticoagulation by automated rotational and vertical movement of the delivery tip, 4) provide subcutaneous tenting so as to create a subcutaneous pocket and keep open (apart) the skin incision edges, 6) provide mechanical abrasion to the wound edges, 7) irrigate the wound. Suction is applied to the shell via an outflow port allowing recovered blood and anticoagulant/irrigant to be withdrawn from the inner chamber.

It is one object of the invention to provide for improved removal of blood from congested tissue through the combination of subcutaneous delivery of anticoagulant and topical recovery.

The device may include an air inlet port allowing the introduction of air into the inner volume and down to the skin surface. Thus, it is another object of the invention to both provide a path of air entry to the skin surface. This air flow will create turbulence in the irrigant flowing through the shell at the skin surface, thus creating mechanical anticoagulation at the skin surface and elsewhere within the shell preventing clot formation.

The device may include a sensor detecting blood volume outflow via the use of weight measurements of the inflow and outflow fluids or optical sensor measurement of outflow concentration.

Thus, it is another object of the invention to provide for semiautomatic operation in which a sensor provides an indication to the operator of successful operation or trigger sequences of agitations and air and liquid flows to provide for efficient blood removal.

The foregoing objects and advantages may not apply to all embodiments of the inventions and are not intended to define the scope of the invention, for which purpose claims are provided. In the following description, reference is made to the accompanying drawings, which form a part hereof, and in which there is shown by way of illustration, a preferred embodiment of the invention. Such embodiment also does not define the scope of the invention and reference must be made therefore to the claims for this purpose.

BRIEF DESCRIPTION OF THE DRAWINGS

FIG. 3 is a fragmentary cross-sectional view similar to that of FIG. 2 showing an alternative embodiment wherein the subcutaneous conduit is attached to a motor for automatic periodic motion;

FIG. 4 is a fragmentary view of FIG. 2 showing the use of an optical sensor for detecting blood outflow such as may be used to control various aspects of the invention;

FIG. 5 is a perspective view similar to that of FIG. 1 showing the addition of a series of needles positioned within the rim of the collection shell for injecting additional anticoagulant around the shell rim at predetermined intervals;

FIG. 8 is a detailed cross-sectional view of the rim of the embodiment of FIG. 6 showing the location of pressure sensitive adhesive on the rim allowing the rim to adhere to the patient's skin and showing partial removal of a release liner protecting that adhesive;

FIG. 9 is a detailed perspective view of the delivery tip of FIG. 7 showing its wedge shape such as provides tenting of the incision; its wide cross-sectional area having multiple orifices for dispersion of anticoagulant and its incorporation of axially extending abrading edges along the outer circumference for breaking up clots; and FIG. 10 is a block diagram of a control unit suitable for the embodiment of FIG. 6 showing provisions for microprocessor control of filtered and actuating air supplies; the anticoagulant and microprocessor monitoring of the flow of recovered anticoagulant and blood.

DETAILED DESCRIPTION OF THE INVENTION

Figure 1:
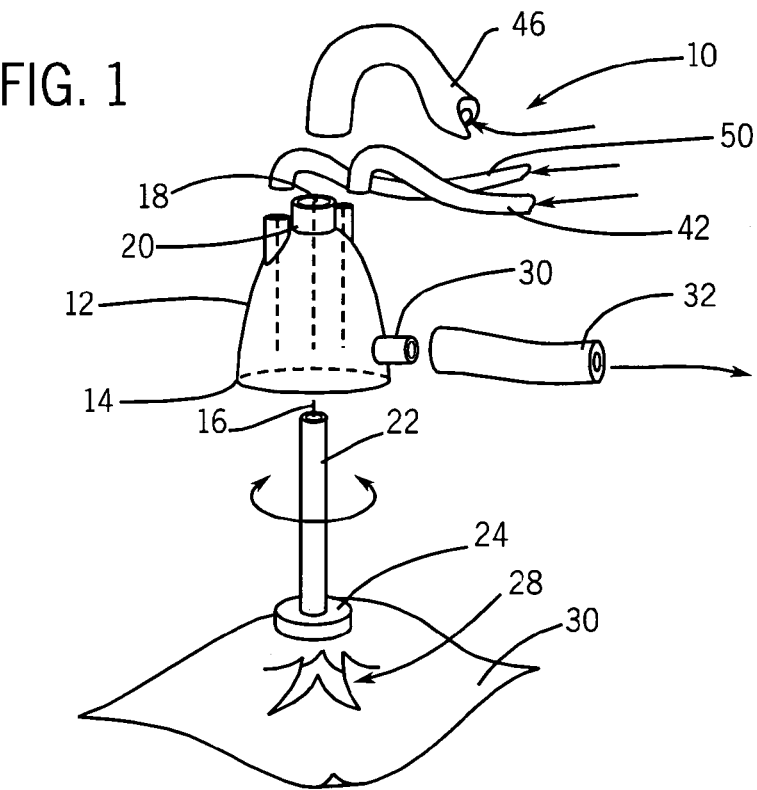
FIG. 1 is an exploded perspective view of the device of the present invention showing its disassembly prior to insertion of a subcutaneous conduit into a cross incision in the patient's skin and the placement of a collection shell over the conduit, and prior to attachment with various input lines and outflow lines.

Referring now to FIG. 1, the device 10 of the present invention includes generally a hollow, bell-shaped shell 12 symmetric generally about vertical axis 16 and having an open lower rim 14. The shell 12 may be constructed of plastic or glass and is preferably of clear material to allow visual inspection of its internal volume.

At the apex of the shell 12 is an opening 18 surrounded by a cylindrical sleeve 20. The sleeve 20 is sized to receive along axis 16, a conduit 22, the latter being preferably a stainless steel tube having a height greater than that of the shell 12. The conduit 22 may freely rotate within the sleeve 20, but blocks the opening 18 to prevent passage of air or liquid into or out of the opening 18 except through the conduit 22.

Figure 2:
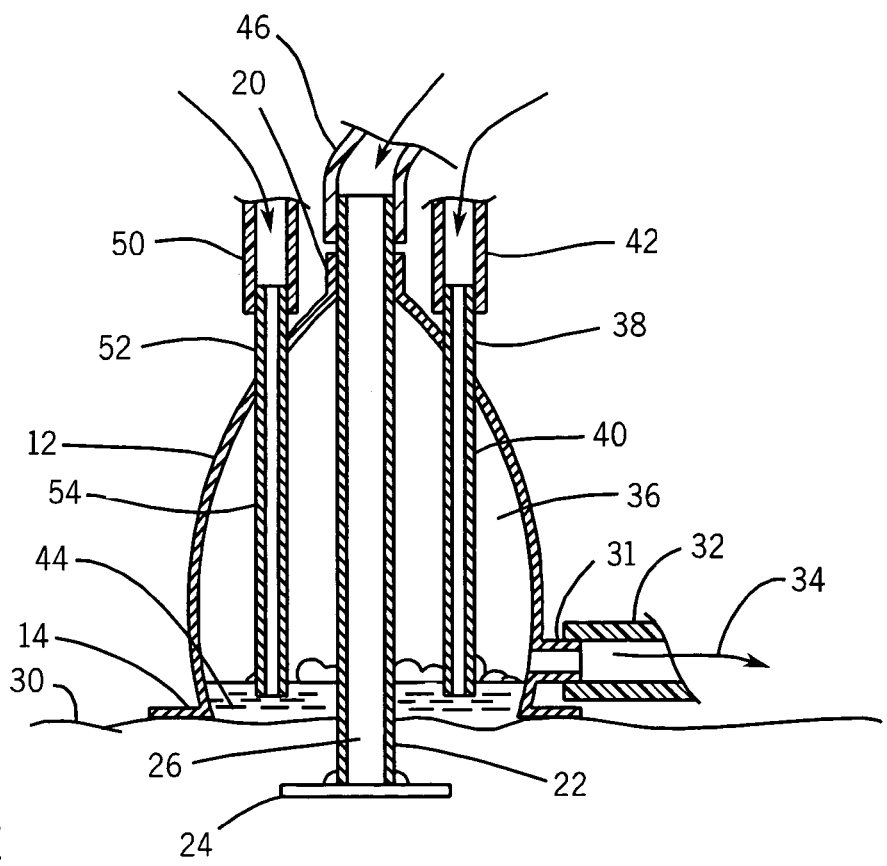
FIG. 2 is an elevational cross sectional view of the device of FIG. 1 assembled and attached to the patient's skin and showing the subcutaneous location of the delivery tip of the conduit formed from a microporous disk (subcutaneous dispenser) and showing the placement of air and irrigation tubes and a suction port on and in the collection shell.

Referring now also to FIG. 2, attached at a lower end of conduit 22 removed from the sleeve 20 is a delivery tip 24 constructed of a microporous disk having an internal structure of pores (not shown) communicating with a central lumen 26 of the conduit 22. The delivery tip 24 is centered on the conduit 22 extending radially therefrom generally perpendicular to axis 16.

A cross incision 28 made in the skin 30 of a patient permits insertion of the delivery tip 24 subcutaneously with the conduit 22 extending upward out of the incision 28. Before insertion of the delivery tip 24' into the incision 28, a small volume bolus of anticoagulant may be administered including possibly other agents such as vasodilators. The portion of the conduit 22 extending out of the incision 28 is received by the sleeve 20 so that the shell 12 moves downward to abut the skin 30 and cover the cross incision 28. The diameter of the rim 14 of the shell 12, in the preferred embodiment, is approximately 1.3 centimeters.

The conduit 22 may be attached at its upper end protruding from the sleeve 20 to an anticoagulant supply hose 46 delivering concentrated heparin or other anticoagulant or thrombolytic substance (such as streptokinase) through the conduit 22 into the microporous delivery tip 24 for diffusion subcutaneously in the surrounding area.

Extending radially near the rim 14 of the shell 12 outside of the shell 12 is an exhaust port 31 sized to receive a suction hose 32 and providing an exhaust path indicated by arrow 34 in FIG. 2 from an inner volume 36 of the shell 12 (defined by the inner walls of the shell 12 and the upper surface of the skin 30) to the suction hose 32. The exhaust port 31 is positioned to draw effluent liquid 44 collecting on the upper surface of the skin 30 out of the shell 12.

An air inlet port 38 extends vertically upward from a top of the shell 12 to receive an air supply hose 42 and to communicate air therefrom through the shell 12 to a central air tube 40 extending downward within the shell to a point immediately above the surface of the skin 30. Ideally the opening of the tube 40 is slightly below the opening of the exhaust port 31 so as to ensure the tip of the air inlet port 38 is immersed in any unexhausted effluent liquid 44.

Similarly, an irrigation port 52 extends vertically upward from a top of the shell 12 opposed to the air inlet port 38 about the sleeve 20 to receive an irrigation hose 50 and to communicate irrigation liquid therefrom through the shell 12 to an irrigation tube 54 similar to the air tube 40 extending downward within the shell to a point immediately above the surface of the skin 30. Tubes 40 and 54 may be stainless steel hypodermic needle tubes.

Referring still to FIGS. 1 and 2, in operation, the delivery tip 24 is first vacuum impregnated with heparin polyvinyl alcohol hydrogel and implanted in the tissue through the cross incision 28 described above. The shell may also be constructed of other materials, such as Teflon or other biocompatible nonthrombogenic substance, with appropriate inset channels to allow subcutaneous delivery of liquid substances. The shell 12 is then be placed over the conduit 22, the latter fitting through sleeve 20, and positioned to cover the incision 28 with the rim 14 resting on the surrounding skin. The rim 14 of the shell 12 is attached to the skin 30 using a surgical adhesive, or an outer flange extension on the shell 12 may be captured beneath the specially designed adhesive strip in the form of an annular ring.

Anticoagulant supply hose 46 is then attached to the portion of the conduit 22 extending out of the shell 12 through sleeve 20, while hoses 32, 42, and 50 may be pre-attached to the shell 12.

Concentrated Heparin, or other substance, is next delivered through the conduit 22 into the microporous delivery tip 24 for diffusion subcutaneously in the surrounding area. Encouraged by the anticoagulant, blood in the region of the delivery tip 24 is drawn up through the incision 28. The extracted blood and anticoagulant then mixes with the irrigant introduced through tube 54. The irrigant is preferably a wash of dilute anticoagulant and saline solution and serves to further inhibit the formation of clots in the resulting effluent liquid 44.

Air entering through an air supply hose 42 through the tube 40 percolates air bubbles through effluent liquid 44, the bubbles serving further to inhibit the formation of clots on the incision surface. Pulsations of pressure, air, and irrigant may also be used to improve blood flow.

Periodically, the conduit 22 is rotated in alternate directions to reduce the formation of clots around the delivery tip 24. The disk shape and its orientation perpendicular to the axis of rotation facilitate this rotational process.

Anticoagulant, irrigation, airflow, and suction are balanced to establish a slight negative pressure within the shell 12 with respect to ambient pressure. The delivery of air, saline and anticoagulant and the application of suction may be performed by an automated control system comprising pumps and pressure transducers and a programmed controller according to techniques well known in the art.

Referring now to FIG. 3 in an alternative embodiment, a stepper motor 55 may be positioned at the apex of the shell 12 so that its shaft 56 is essentially coaxial with axis 16 and conduit 22. The shaft 56 may be hollow to permit passage of anticoaguilant therethrough and the lower portion of the shaft may extend through the opening 18 to be attached to the conduit 22. The opposite, upper end of the shaft 56 may be attached to anticoagulant supply hose 46. Signals received through motor wires 58 from an automatic controller of a type well known in the art may drive the motor to produce a periodic reciprocating motion of the conduit 22 to eliminate the need for manual intervention.

Referring now to FIG. 4, an optical sensor 60 may be fit within the wall of the shell 12 to detect color changes in the effluent liquid 44 collecting in the lower portion of the shell adjacent to the skin 30. Ideally, the sensor 60 is placed near the exhaust port 31 (not shown in FIG. 4) and may include, for example, a light emitter (such as a light emitting diode) and light detector (such as a photo transistor) for evaluating the color or reflectance of the effluent liquid 44. This measurement may be used to indicate the amount of blood outflow so as to provide a signal through a controller 62 either to attending personnel that rotation of the conduit 22 is required, or an inspection of the device is required, or to automatically actuate changes in the air flow, irrigation flow, or mechanical agitation the conduit through the motor shown in FIG. 3.

Referring now to FIG. 5 in an additional embodiment, the shell 12 may support a set of vertically disposed hypodermic needles 64 generally parallel to the conduit 22 and spaced at regular angular intervals about the conduit 22 just inside the rim 14 and extending a distance 66 below the rim 14 to provide for the injection of additional anticoagulant subcutaneously around the delivery tips 24.

Figure 6:
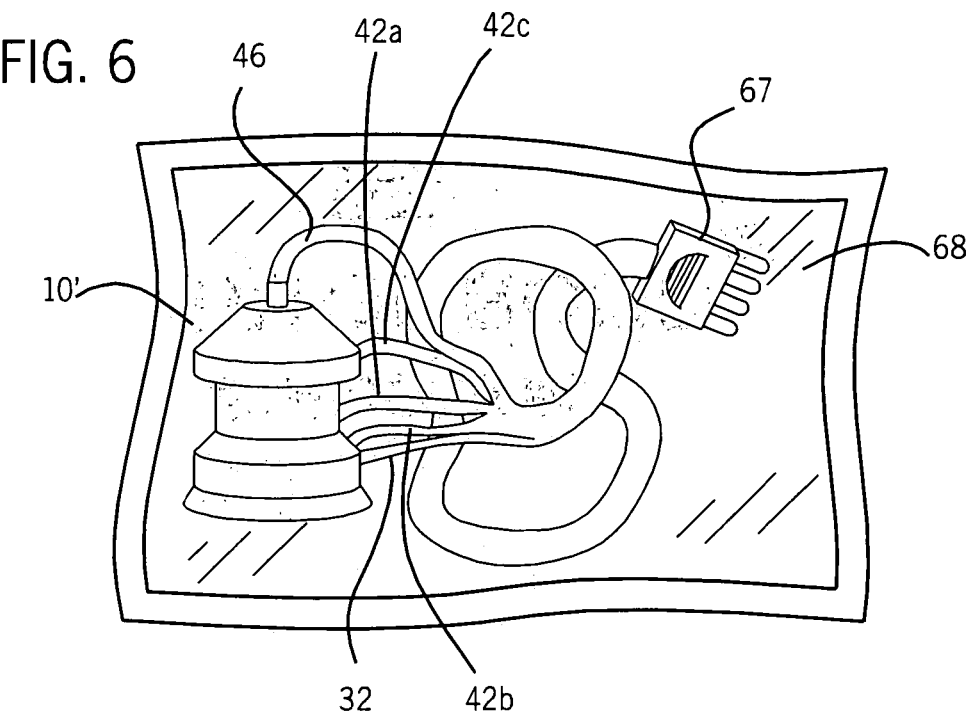
FIG. 6 is a perspective view of a kit version of an alternative embodiment of the device of FIG. 1 showing the shell assembly as attached to supply and return lines terminating in a multi-line connector and housed in a sterile package for one time use.

Referring now to FIG. 6, in an additional embodiment, the device 10' may be pre-assembled to the necessary hoses including air supply hoses 42a, 42b, and 42c, as will be described, anticoagulant supply hose 46, and the suction hose 32. Each of these separate hoses may be joined into a single bundle terminating in a multi-hose connector 67 that may be used to rapidly connect the device 10' to the controller 62. This pre-assembled device 10' and hoses may be sterilized and packaged in sterile condition within a sealed pouch 68 for ready access by the physician.

Figure 7:
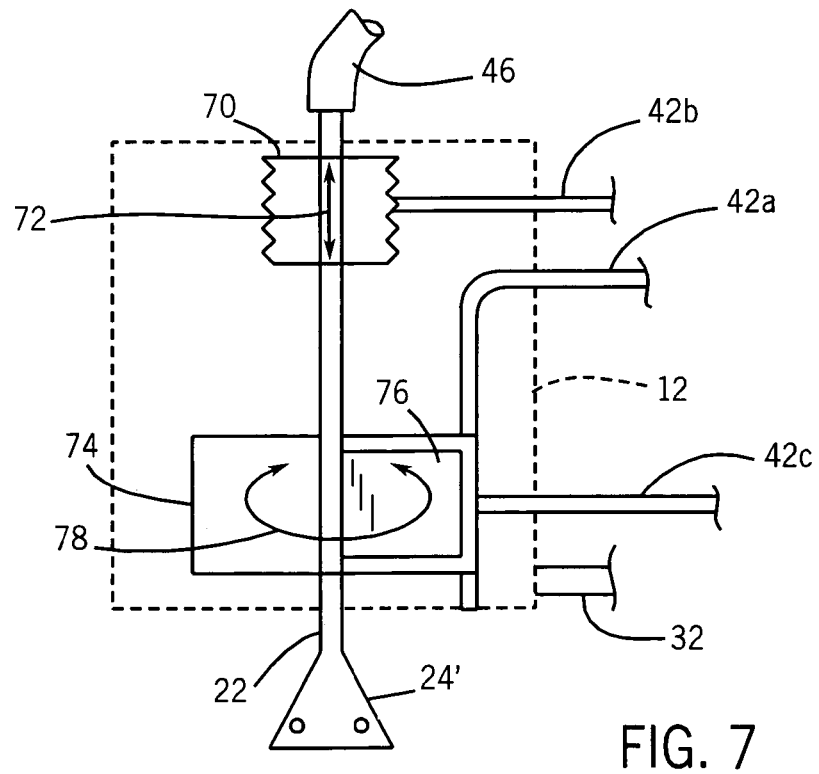
FIG. 7 is a simplified, block diagram of the embodiment of FIG. 6 showing the relationship of pneumatic axial and pneumatic rotational actuators for combined rotational and axial movement of the conduit and showing an alternative delivery tip.

Referring now to FIG. 7, the embodiment of FIG. 6 may differ from the previously described embodiment of FIG. 2 by elimination of the irrigation hose 50 and the addition of two additional air supply hoses 42b and 42c to supplement the air supply hose 42a, the latter which corresponds to air supply hose 42 of FIG. 2.

As before, the anticoagulant supply hose 46 attaches to conduit 22 to deliver anticoagulant to delivery tip 24'.

Air supply hose 42b provides air to bellows actuator 70 having one portion attached to the shell 12 and the other portion attached to the conduit 22 to cause axial motion 77 of the conduit 22 under varying air pressure from air supply hose 42b. The axial motion moves delivery tip 24 into and out of the incision to reduce clot formation and to promote bleeding by tenting or flexing of the edges of the incision 28 with the upper part of the delivery tip 24 as will be described. The tenting effect keeps the edges of the wound separated allowing the irrigant to irrigate the entire wound and flow freely to the skin surface.

Air supply hose 42c provides air to a rotary actuator 74 having an internal vane 76 attached to the conduit 22 to provide rotary motion 78 of the conduit 22 back and forth about its axis. These two motions 77 and 78 may be combined to produce a spiraling up and down motion further preventing clot formation.

Referring now to FIG. 9, the delivery tip 24' may have a frusto-conical shape with its smaller base facing upward toward the shell 12. The central lumen 26 of the conduit 22 passes through the narrow top of the delivery tip 24' and opens into a plurality of ports 84 extending out the wider periphery of the lower portion of the delivery tip 24' to better disperse anticoagulant.

The delivery tip may be constructed of a biologically inert material such as Teflon and attached to the conduit 22 so that its point extends through the incision 28. The wedge shape of the delivery tip 24' plus the up and down reciprocal action 72 flexes the edges of the incision 28 laterally in and out so as to prevent clot formation and promote bleeding.

Extending upward from the lower base of the delivery tip 24' are grooves providing axial abrading edges 82. The rotational movement 78 causes the axial abrading edges 82 to disrupt clot formation and further abrade and promote bleeding.

Referring now to FIG. 8, a lower planar surface of the rim 14 of the shell 12 may be covered with a pressure sensitive adhesive 86 protected initially by a release liner 88. The release liner 88 may be peeled back so that the pressure sensitive adhesive 86 is exposed. In this way, when the rim 14 is pressed against the skin 30, the pressure sensitive adhesive 86 holds the shell 12 in place prior to the creation of a vacuum as has been described. In this embodiment, the shell 12 may be constructed of a lightweight plastic such as polyethylene.

Referring now to FIG. 10, the controller 62 for the embodiment of FIG. 6 may be self-contained so as to hang on an "IV" pole or the like by hook 89 to attach to the device 10' and hoses 42a, 42b, 42c, 46, and 32 via a multi-line connector 90 compatible with multi-hose connector 67. The controller 62 provides for central control of air, anticoagulant, and suction through a microprocessor 100.

Air may be provided from a pressurized hospital source 92 or via a self contained pump 94 communicating with room air. The air feeding air supply hose 42a is micro-filtered by filter 99 to provide a sterile air stream for agitation of the removed anti-coagulant and blood as has been described. This in turn allows for autotransfusion of the recaptured blood as will be described. Air supply hoses 42b and 42c need not be filtered provided their associated actuators 70 and 74 do not exhaust air into the shell 12.

Each of the air supply hoses 42a, 42b, and 42c pass through electrically controllable valves 96 allowing air flow to be metered by microprocessor 100. The valves 96 on air supply hoses 42b and 42a allow control of the motion of the conduit in rotation and axial translation such as may optimized to minimize damage and maximize the therapeutic effect of this motion. As will be described, this motion may be controlled according to the flow of blood and anticoagulant back to the controller 62 to create a control closed loop system.

Anticoagulant may be provided from an IV bag 104 such as may be hung on the IV pole flowing under gravity or pumped by internal pump 102 controlled by the microprocessor 100. The anticoagulant passes through a metering valve 110 (or is controlled by a metering pump 102) allowing the microprocessor 100 to control flow of anticoagulant to the anticoagulant supply hose 46.

Suction for the suction hose 32 may come from an internal suction pump 112 or may be provided by a connection to the hospital vacuum line 114. The suction hose 32 passes through a flow meter 106 measuring the flow of returned anticoagulant and blood such as may provide a signal to the microprocessor 100 to control the amount of agitation by means of air supply hoses 42b and 42c as described above. Ideally, the rate of change of blood volume over time is used to determine the frequency of the actuation.

The returned blood and anticoagulant may-be collected in a reservoir 116 attached to the IV pole for later autotransfusion.

In the preferred embodiment, the controller 62 monitors on a continuous basis, the amount of blood and anticoagulant removed from the incision as measured by the flow meter 106 or by a weighing system employing well known strain gauge or other type of weighing systems. The amount of blood alone may be determined by subtracting the amount of anticoagulant delivered by anticoagulant supply hose 46 through metering valve 110 and this information is displayed to the operator to provide a quantitative indication of the correct operation of the device 10'.

The controller 62 may include a battery 118 and/or provision for connection to a low voltage cabling to a transformer attached to the hospital line voltage.

It is specifically intended that the present invention not be limited to the embodiments and illustrations contained herein, but that modified forms of those embodiments including portions of the embodiments and combinations of elements of different embodiments also be included as come within the scope of the following claims.

We claim:

1. A device for the treatment of venous congestion or venous stasis comprising:
    a shell having a rim adapted to abut a patient's skin to define a suction area circumscribed by the rim and enclosed by an inner volume of the shell;
    a conduit supported by the shell and having a delivery tip at a distal end of the conduit the delivery tip including a blunt distal disc-shaped end comprising a microporous material and having a cross-sectional area for dispensing fluid over an area that is larger than a lumen of the conduit, the delivery tip being positionable subcutaneously through an existing incision in the skin and below the rim within the suction area when the shell is positioned against the patient's skin to diffuse an anticoagulant or a thrombolytic agent beneath the skin; and
    a suction port attached to the shell through which recovered anticoagulant and blood may be drawn from the inner volume.

2. The device of claim 1 wherein the delivery tip includes a plurality of openings through which anticoagulant may pass.

3. The device of claim 1 wherein the delivery tip is made of a biocompatible non-thrombogenic substance.

4. The device of claim 1 wherein the conduit is supported by the shell to permit axial rotation of the conduit.

5. The device of claim 1 wherein the conduit is supported by the shell to permit axial translation of the conduit.

6. The device of claim 1 including further an air inlet port allowing the introduction of air to a region proximate to the patient's skin to agitate liquid at the patient's skin.

7. The device of claim 1 including further a sensor detecting blood outflow.

8. A device for the treatment of venous congestion or venous stasis comprising:
    a shell having a rim adapted to abut a patient's skin to define a suction area circumscribed by the rim and enclosed by an inner volume of the shell;
    a conduit supported by the shell and having a blunt delivery tip at a distal end of the conduit for the delivery of anticoagulant or thrombolytic agent positionable subcutaneously through an existing incision in the skin below the rim within the suction area when the shell is positioned against the patient's skin, the delivery tip including a subcutaneous dispenser extending perpendicularly to the conduit and having a cross-sectional area for dispensing fluid that is larger than a lumen of the conduit to disperse the anticoagulant beneath the skin; and
    a suction port attached to the shell through which recovered anticoagulant and blood may be drawn from the inner volume.

9. The device of claim 8, wherein the delivery tip comprises a microporous material.

10. The device of claim 8, wherein the delivery tip is disc-shaped.

11. The device of claim 8, wherein the delivery tip is frusto-conical in shape.

12. The device of claim 11, wherein the delivery tip includes a plurality of ports for dispensing fluid.

* * * * *

UNITED STATES PATENT AND TRADEMARK OFFICE
CERTIFICATE OF CORRECTION

PATENT NO. : 7,479,124 B2
APPLICATION NO. : 10/273215
DATED : January 20, 2009
INVENTOR(S) : Gregory K. Hartig et al.

It is certified that error appears in the above-identified patent and that said Letters Patent is hereby corrected as shown below:

Column 1, line 14
Under the heading "STATEMENT REGARDING FEDERALLY SPONSORED RESEARCH OR DEVELOPMENT" please add the following:
-- This invention was made with United States government support awarded by the following agency: NIH HL69553. The United States government has certain rights in this invention. --

Column 5, line 18
"anticoaguilant" should be -- anticoagulant --

Signed and Sealed this

Fourteenth Day of April, 2009

JOHN DOLL
*Acting Director of the United States Patent and Trademark Office*